(12) United States Patent
Matsuda et al.

(10) Patent No.: US 6,500,976 B2
(45) Date of Patent: Dec. 31, 2002

(54) ORGANOSILICON COMPOUNDS

(75) Inventors: Takashi Matsuda, Gunma-ken (JP);
Mikio Shiono, Gunma-ken (JP);
Kenichi Fukuda, Gunma-ken (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 0 days.

(21) Appl. No.: 09/970,685

(22) Filed: Oct. 5, 2001

(65) Prior Publication Data

US 2002/0087019 A1 Jul. 4, 2002

(30) Foreign Application Priority Data

Oct. 5, 2000 (JP) ........................................ 2000-306309

(51) Int. Cl.$^7$ .................................................. C07F 7/08
(52) U.S. Cl. ........................ 556/431; 556/434; 556/435; 549/214
(58) Field of Search .......................... 549/214; 556/434, 556/435, 431

(56) References Cited

U.S. PATENT DOCUMENTS 5,117,001 A * 5/1992 Okinoshima et al. ....... 549/214
5,362,887 A * 11/1994 Shiobara et al. ............ 549/214

* cited by examiner

*Primary Examiner*—Paul F. Shaver
(74) *Attorney, Agent, or Firm*—Birch, Stewart, Kolasch & Birch, LLP

(57) ABSTRACT

Organosilicon compounds each having in a molecule (A) a perfluoroalkyl group of at least 3 carbon atoms which may be separated by an etheric oxygen atom, (B) a monovalent hydrocarbon group containing a carboxylic acid anhydride structure, and (C) a hydrosilyl (SiH) group are novel and added to thermosetting elastomer compositions as adhesion aids whereby the compositions are improved in adhesion to various materials including metals, alloys, plastics, and ceramics.

8 Claims, No Drawings

ORGANOSILICON COMPOUNDS

BACKGROUND OF THE INVENTION

1. Technical Field

This invention relates to novel organosilicon compounds which are added to various thermosetting elastomer compositions as adhesive aids.

2. Background Art

Known adhesive aids added to conventional thermosetting elastomer compositions include those having alkoxysilyl groups, acid anhydride groups and SiH groups. Although some adhesive aids achieve good adherence, there is a desire to have compounds more effective as adhesive aids.

SUMMARY OF THE INVENTION

It has been found that organosilicon compounds having in a molecule (A) a perfluoroalkyl group of at least 3 carbon atoms which may be separated by an etheric oxygen atom, (B) a monovalent hydrocarbon group containing a carboxylic acid anhydride structure, and (C) a hydrosilyl group are effective as adhesive aids, especially as adhesive aids in elastomer compositions containing fluorinated compounds for enhancing their adhesion to metals.

DESCRIPTION OF THE PREFERRED EMBODIMENTS

The organosilicon compound of the invention has in a molecule (A) a perfluoroalkyl group of at least 3 carbon atoms which may be separated by an etheric oxygen atom, (B) a monovalent hydrocarbon group containing a carboxylic acid anhydride structure, and (C) a hydrosilyl (SiH) group.

Specifically, the organosilicon compound has the average compositional formula (1) and preferably the general formula (2), (3) or (4).

$$Rf_a R^1_b R^2_c H_d SiO_{(4-a-b-c-d)/2} \quad (1)$$

In formula (1), Rf is a monovalent organic group containing a perfluoroalkyl group of at least 3 carbon atoms which may be separated by an etheric oxygen atom, $R^1$ is a substituted or unsubstituted monovalent hydrocarbon group, $R^2$ is a monovalent hydrocarbon group containing a carboxylic acid anhydride structure, a, b, c and d are numbers satisfying:
0.01≦a≦50.5, preferably 0.05≦a≦0.3,
0≦b≦2, preferably 0.5≦b≦1.5,
0.01≦c≦0.5, preferably 0.05≦c≦0.3,
0.01≦d≦0.5, preferably 0.05≦d≦0.3, and
2≦a+b+c+d≦3.

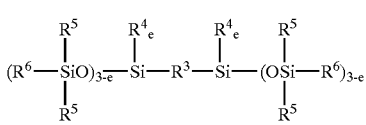

(2)

In formula (2), $R^3$ is a substituted or unsubstituted divalent hydrocarbon group, $R^4$ and $R^5$ each are a substituted or unsubstituted monovalent hydrocarbon group, $R^6$ is independently hydrogen, Rf, $R^1$ or $R^2$, wherein Rf, $R^1$ and $R^2$ are as defined above, at least one hydrogen, at least one Rf and at least one $R^2$ are contained in a molecule, and e is an integer of 0 or 1.

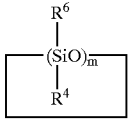

(3)

In formula (3), $R^4$ is a substituted or unsubstituted monovalent hydrocarbon group; $R^6$ is independently hydrogen, Rf, $R^1$ or $R^2$, wherein Rf, $R^1$ and $R^2$ are as defined above; at least one hydrogen, at least one Rf and at least one $R^2$ are contained in a molecule; and m is a positive integer of at least 3 and preferably 3 to 8.

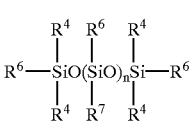

(4)

In formula (4), $R^4$ is a substituted or unsubstituted monovalent hydrocarbon group; $R^6$ is independently hydrogen, Rf, $R^1$ or $R^2$, wherein Rf, $R^1$ and $R^2$ are as defined above; at least one hydrogen, at least one Rf and at least one $R^2$ are contained in a molecule; n is a positive integer of at least 1, preferably 1 to 500 and more preferably 5 to 200; and $R^7$ is $R^4$ or a group of the following formula (5):

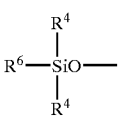

(5)

wherein $R^4$ and $R^6$ are as defined above.

More illustratively, the substituted or unsubstituted monovalent hydrocarbon groups represented by $R^1$, $R^4$ and $R^5$ are preferably those of 1 to 12 carbon atoms, more preferably 1 to 8 carbon atoms, for example, alkyl groups such as methyl, ethyl and propyl, cycloalkyl groups such as cyclohexyl, aryl groups such as phenyl and tolyl, and the foregoing groups in which some hydrogen atoms are substituted with halogen atoms.

The monovalent hydrocarbon group containing a carboxylic acid anhydride structure, represented by $R^2$, is not critical as long has it has a carboxylic acid anhydride structure. Groups of the following formula are preferred.

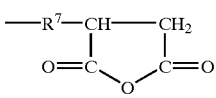

Herein $R^7$ is a divalent hydrocarbon group having 1 to 15 carbon atoms, and especially 2 to 10 carbon atoms, for example, an alkylene or alkenylene group.

Illustrative examples are given below.

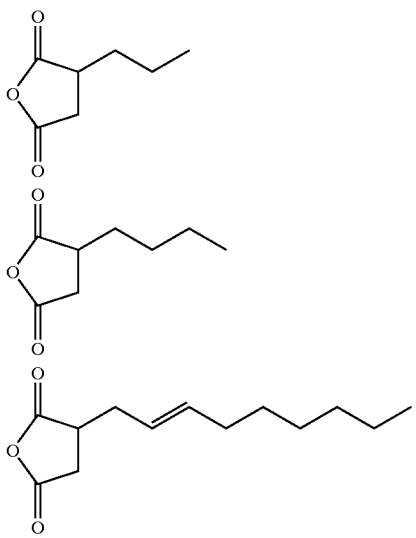

The substituted or unsubstituted divalent hydrocarbon groups represented by $R^3$ are preferably those of 1 to 12 carbon atoms, more preferably 1 to 8 carbon atoms, for example, alkylene groups such as methylene, ethylene and propylene, cycloalkylene groups such as cyclohexylene, arylene groups such as phenylene, and the foregoing groups in which some hydrogen atoms are substituted with halogen atoms.

The monovalent organic groups containing a perfluoroalkyl group of at least 3 carbon atoms which may be separated by an etheric oxygen atom, represented by Rf, include $F(C_xF_{2x})CH_2CH_2—$,
$F(C_xF_{2x})CH_2CH_2CH_2—$, and
$F(C_yF_{2y}O)_pC_zF_{2z}—A—$, wherein x is 3 to 20, y is 1 to 4, z is 1 to 10, p is 1 to 100, y multiplied by p is at least 2, and A is a divalent organic group, for example, an alkylene group such as methylene, ethylene or propylene.

Illustrative, non-limiting examples of the organic groups represented by Rf are given below. Note that Me is methyl.

$C_4F_9CH_2CH—$
$C_8F_{17}CH_2CH_2CH_2—$

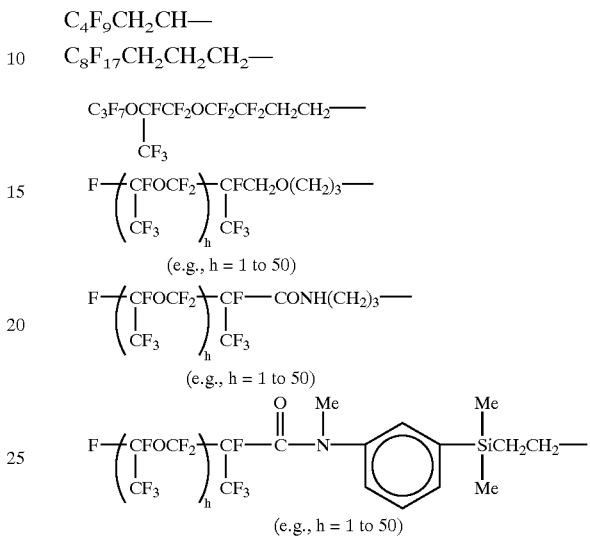

$C_3F_7O(CF_2CF_2CF_2O)_hCF_2CF_2CH_2CH_2—$ (e.g., h=1 to 50)

$F—(CF_2O)_h(CF_2CF_2O)_iCF_2CH_2CH_2—$ (e.g., h=1 to 50, i=1 to 50)

Illustrative examples of the organosilicon compounds according to the invention are given below. They are typical examples, and the inventive compounds are not limited thereto. Note that Me is methyl.

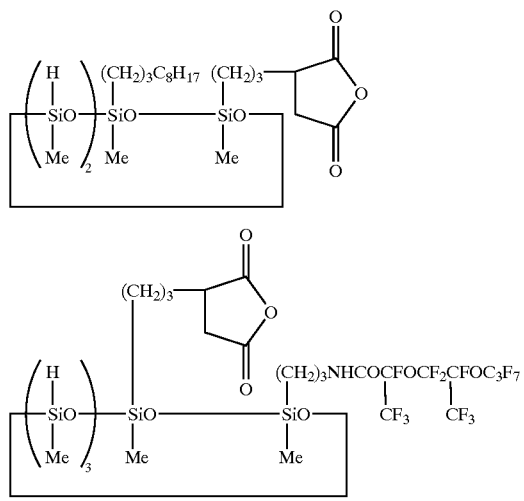

-continued

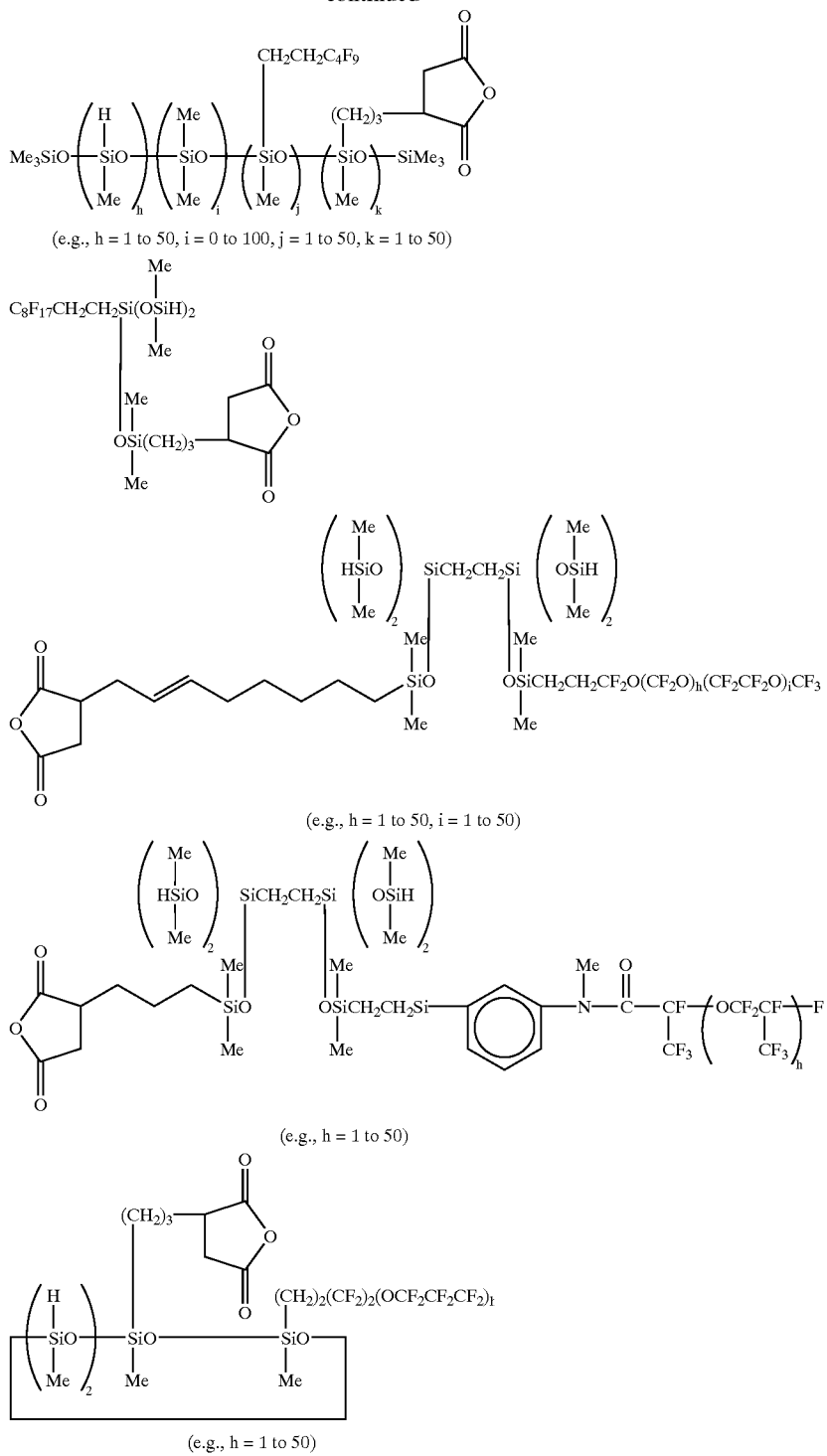

The organosilicon compounds of the invention can be synthesized, for example, by the following method. The starting compound is an organosilicon compound having fluorine-modified groups, represented by the formula:

$$Rf_a R^1{}_b H_d SiO_{(4-a-b-d)/2}$$

wherein Rf and $R^1$ are as defined above, and $0.01 \leq a \leq 0.5$, $0 \leq b \leq 2$, $0.01 \leq d \leq 0.5$, and $2 \leq a+b+d \leq 3$. By effecting addition or hydrosilylation reaction of an acid anhydride having an ethylenically unsaturated group to the organosilicon compound having fluorine-modified groups in the presence of a hydrosilylation catalyst such as a platinum complex compound, the end compound is obtainable.

The reaction temperature is usually about 50 to 150° C., preferably about 70 to 120° C. If necessary, the reactants are diluted with a solvent such as toluene, xylene or 1,3-bistrifluoromethylbenzene.

Most often, the organosilicon compounds of the invention are added to thermosetting elastomer compositions as adhesion aids whereby the compositions are improved in adhesion to various materials including metals and alloys such as aluminum, iron, stainless steel, nickel alloys, chromium alloys and copper alloys, plastics such as acrylic resins, nylon, PPS, PBT, PET, epoxy resins, polyimides and polyvinyl chloride, and ceramics such as alumina and silicon nitride.

EXAMPLE

Examples of the invention are given below by way of illustration and not by way of limitation. Me is methyl.

Example 1

A 300-ml four-necked flask equipped with a stirrer, thermometer, reflux condenser and dropping funnel was charged with 70.0 g of an organosilicon compound of structure (i) below and 35.0 g of 1,3-bistrifluoromethylbenzene and heated to an internal temperature of 80° C.

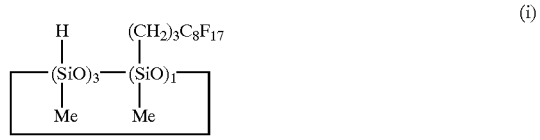

(i)

Then, 0.02 g of a toluene solution of the complex of chloroplatinic acid with 1,3-divinyl-1,1,3,3-tetramethyldisiloxane (concentration 0.5 wt % calculated as platinum metal) was added to the flask, and 14.0 g of allylsuccinic anhydride was added dropwise from the dropping funnel.

After the completion of dropwise addition, the reaction solution was ripened at 80° C. for one hour. After the consumption of allylsuccinic anhydride was confirmed by gas chromatography, the solution was cooled.

Thereafter, 1.0 g of activated carbon was added to the solution, which was stirred for one hour and filtered. The filtrate was stripped at 120° C./3 mmHg for removing the solvent, leaving 74.3 g of a colorless clear liquid (viscosity 335 cs, specific gravity 1.393, refractive index 1.389).

On analysis by $^1$H-NMR, IR and elemental analysis, the liquid was identified to be the following compound (ii).

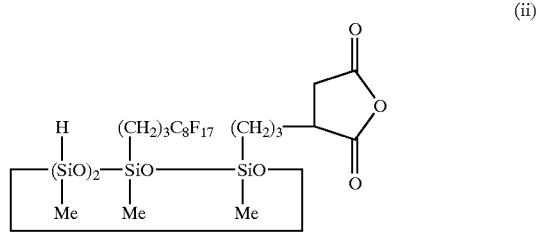

(ii)

$^1$H-NMR

δ 60.25(s, Si—$\underline{CH_3}$: 12H)

δ 60.75(m, Si—$\underline{CH_2}$—: 4H)

δ 1.6 to 2.4(m, Si—CH$_2$—$\underline{CH_2}$—$\underline{CH_2}$—: 8H)

δ 2.63(m, CO—CH: 1H)

δ 3.18(m, CO—CH$_2$—: 2H)

δ 4.85(s, Si—H: 2H)

IR 1788, 1865 cm$^{-1}$ $\nu_{C=O}$ 2170 cm$^{-1}$ $\nu_{Si-H}$

| Elemental analysis | | | | | |
|---|---|---|---|---|---|
| | C | H | O | Si | F |
| Found (%) | 31.7 | 3.2 | 13.5 | 13.3 | 38.3 |
| Calcd. (%) | 31.4 | 3.5 | 13.3 | 13.3 | 38.5 |

Example 2

A 300-ml four-necked flask equipped with a stirrer, thermometer, reflux condenser and dropping funnel was charged with 70.0 g of an organosilicon compound of structure (iii) below and 35.0 g of 1,3-bistrifluoromethylbenzene and heated to an internal temperature of 80° C.

(iii)

Then, 0.02 g of a toluene solution of the complex of chloroplatinic acid with 1,3-divinyl-1,1,3,3-tetramethyldisiloxane (concentration 0.5 wt % calculated as platinum metal) was added to the flask, and 14.0 g of allylsuccinic anhydride was added dropwise from the dropping funnel.

After the completion of dropwise addition, the reaction solution was ripened at 80° C. for one hour. After the consumption of allylsuccinic anhydride was confirmed by gas chromatography, the solution was cooled.

Thereafter, 1.0 g of activated carbon was added to the solution, which was stirred for one hour and filtered. The filtrate was stripped at 120° C./3 mmHg for removing the solvent, leaving 75.2 g of a colorless clear liquid (viscosity 92 cs, specific gravity 1.375, refractive index 1.385).

On analysis by $^1$H-NMR, IR and elemental analysis, the liquid was identified to be the following compound (iv).

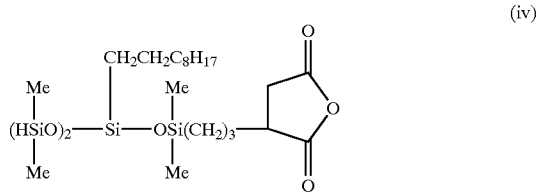

(iv)

$^1$H-NMR

δ 0.09(s, C—Si—$\underline{CH_3}$: 6H)

δ 0.16(s, H—Si—$\underline{CH_3}$: 12H)

δ 0.65(m, Si—$\underline{CH_2}$—CH$_2$—CH$_2$—: 2H)

δ 0.72(m, Si—$\underline{CH_2}$—CH$_2$—CF$_2$—: 2H)

δ 1.4 to 2.2(m, Si—CH$_2$—$\underline{CH_2}$—$\underline{CH2}$— and Si—CH$_2$—$\underline{CH_2}$—CF$_2$—: 6H)

δ 2.52(m, CO—CH: 1H)

δ 3.01(m, CO—CH$_2$—: 2H)

δ 4.72(s, Si—H: 2H)

IR 1787, 1867 cm$^{-1}$ $\nu_{C=O}$ 2133 cm$^{-1}$ $\nu$Si—H

| | Elemental analysis | | | | |
|---|---|---|---|---|---|
| | C | H | O | Si | F |
| Found (%) | 32.2 | 3.8 | 11.1 | 13.6 | 39.3 |
| Calcd. (%) | 32.9 | 3.9 | 11.4 | 13.3 | 38.5 |

Example 3

A 300-ml four-necked flask equipped with a stirrer, thermometer, reflux condenser and dropping funnel was charged with 100.0 g of an organosilicon compound of structure (v) below (SiH group content 0.10 mol) and 50.0 g of 1,3-bistrifluoromethylbenzene and heated to an internal temperature of 80° C.

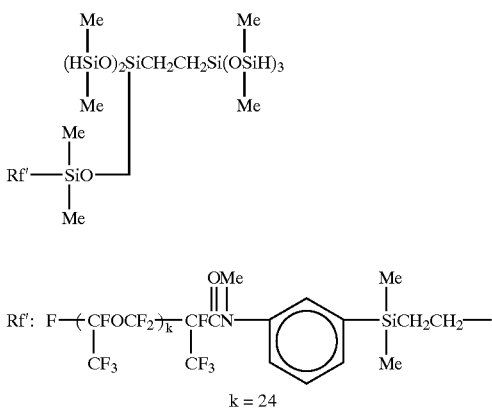

(v)

Then, 0.02 g of a toluene solution of the complex of chloroplatinic acid with 1,3-divinyl-1,1,3,3-tetramethyl-disiloxane (concentration 0.5 wt % calculated as platinum metal) was added to the flask, and 2.8 g (0.020 mol) of allylsuccinic anhydride was added dropwise from the dropping funnel.

After the completion of dropwise addition, the reaction solution was ripened at 80° C. for one hour. After the consumption of allylsuccinic anhydride was confirmed by gas chromatography, the solution was cooled.

Thereafter, 1.5 g of activated carbon was added to the solution, which was stirred for one hour and filtered. The filtrate was stripped at 120° C./3 mmHg for removing the solvent, leaving 95.3 g of a colorless clear liquid (viscosity 25,000 cp, specific gravity 1.664, refractive index 1.343).

On analysis by $^1$H-NMR, IR and elemental analysis, the liquid was identified to be the following compound (vi).

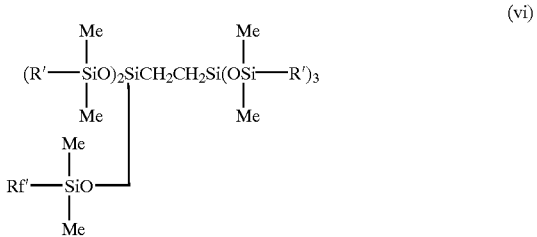

(vi)

Note that of five R' groups, on the average, four are R'=H, and one is

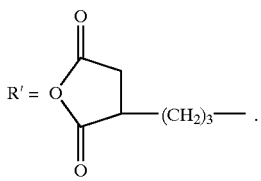

$^1$H-NMR

δ 0.09(S, C—Si—CH$_3$: 12H)

δ 0.16(s, H—Si—CH$_3$: 24H)

δ 0.31(s, arom.—Si—CH$_3$: 6H)

δ 0.6 to 1.3(m, Si—CH$_2$—: 10H)

δ 1.4 to 2.2(m, Si—CH$_2$—CH$_2$—CH$_2$—: 4H)

δ 2.52(m, CO—CH: 1H)

δ 3.01(m, CO—CH$_2$—: 2H)

δ 3.23(s, N—CH$_3$: 3H)

δ 4.72(s, Si—H: 4H)

δ 7.2 to 7.7(m, arom.: 4H)

IR 1788, 1865 cm$^{-1}$ν$_{C=O}$ 2130 cm$^{-1}$ν$_{Si—H}$

| | Elemental analysis | | | | | |
|---|---|---|---|---|---|---|
| | C | H | O | Si | F | N |
| Found (%) | 25.4 | 1.3 | 10.8 | 5.1 | 57.1 | 0.3 |
| Calcd. (%) | 25.7 | 1.4 | 10.9 | 5.0 | 56.7 | 0.3 |

Japanese Patent Application No. 2000-306309 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. An organosilicon compound having the average compositional formula (1):

$$Rf_aR^1{}_bR^2{}_cH_dSiO_{(4-a-b-c-d)/2} \qquad (1)$$

wherein

Rf is a monovalent organic group containing a perfluoroalkyl group of at least 3 carbon atoms which may be separated by an etheric oxygen atom, R$^1$ is a substituted or unsubstituted monovalent hydrocarbon group, R$^2$ is a monovalent hydrocarbon group containing a carboxylic acid anhydride structure, and a, b, c, and d are numbers satisfying the relationships 0.01≦a≦0.5, 0≦b≦2, 0.01≦c≦0.5, 0.01≦d≦0.5, and 2≦a+b+c+d≦3.

2. An organosilicon compound having the general formula (2):

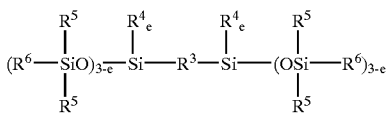

(2)

wherein
- Rf is a monovalent organic group containing a perfluoroalkyl group of at least 3 carbon atoms which may be separated by an etheric oxygen atom,
- $R^1$ is a substituted or unsubstituted monovalent hydrocarbon group,
- $R^2$ is a monovalent hydrocarbon group containing a carboxylic acid anhydride structure,
- $R^3$ is a substituted or unsubstituted divalent hydrocarbon group,
- $R^4$ and $R^5$ each are a substituted or unsubstituted monovalent hydrocarbon group,
- $R^6$ is independently hydrogen, Rf, $R^1$, or $R^2$, at least one hydrogen, Rf, and $R^2$ each being contained in a molecule, and
- e is an integer of 0 or 1.

3. An organosilicon compound having the general formula (3) or (4):

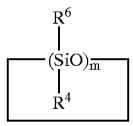

(3)

wherein
- $R^4$ is a substituted or unsubstituted monovalent hydrocarbon group;
- Rf is a monovalent organic group containing a perfluoroalkyl group of at least 3 carbon atoms which may be separated by an etheric oxygen atom,
- $R^1$ is a substituted or unsubstituted monovalent hydrocarbon group,
- $R^2$ is a monovalent hydrocarbon group containing a carboxylic acid anhydride structure,
- $R^6$ is independently hydrogen, Rf, $R^1$, or $R^2$, at least one hydrogen, Rf, and $R^2$ each being contained in a molecule; and
- m is a positive integer of at least 3, and

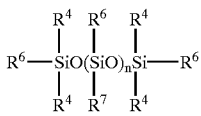

(4)

wherein
- $R^4$ is a substituted or unsubstituted monovalent hydrocarbon group;
- Rf is a monovalent organic group containing a perfluoroalkyl group of at least 3 carbon atoms which may be separated by an etheric oxygen atom,
- $R^1$ is a substituted or unsubstituted monovalent hydrocarbon group,
- $R^2$ is a monovalent hydrocarbon group containing a carboxylic acid anhydride structure,

- $R^6$ is independently hydrogen, Rf, $R^1$, or $R^2$, at least one hydrogen, Rf, and $R^2$ each being contained in a molecule;
- n is a positive integer of at least 1; and
- $R^7$ is $R^4$ or a group of the following formula (5):

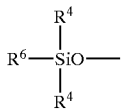

(5)

wherein $R^4$ and $R^6$ are as defined above.

4. The organosilicon compound of claim 1, wherein Rf is $F(C_xF_{2x})CH_2CH_2-$, $F(C_xF_{2x})CH_2CH_2CH_2-$, or $F(C_yF_{2y}O)_pC_zF_{2z}-A-$ in which x is 3 to 20, y is 1 to 4, z is 1 to 10, p is 1 to 100, y multiplied by p is at least 2, and A is a divalent alkylene group,
$R^1$ has 1 to 8 carbon atoms, and
$R^2$ is a group of the formula

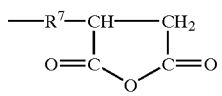

wherein $R^7$ is a divalent hydrocarbon group having 2 to 10 carbon atoms.

5. The organosilicon compound of claim 3, wherein
Rf is $F(C_xF_{2x})CH_2CH_2-$, $F(C_xF_{2x})CH_2CH_2CH_2-$, or $F(C_yF_{2y}O)_pC_zF_{2z}-A-$ in which x is 3 to 20, y is 1 to 4, z is 1 to 10, p is 1 to 100, y multiplied by p is at least 2, and A is a divalent alkylene group,
$R^1$ has 1 to 8 carbon atoms, and
$R^2$ is a group of the following formula wherein $R^7$ is a divalent hydrocarbon group having 2 to 10 carbon atoms

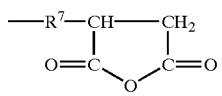

$R^3$ has 1 to 8 carbon atoms,
$R^4$ has 1 to 8 carbon atoms, and
$R^5$ has 1 to 8 carbon atoms.

6. The organosilicon compound of claim 3, having the formula (3) wherein
$R^4$ is a substituted or unsubstituted monovalent hydrocarbon group of 1 to 8 carbon atoms;
Rf is a monovalent organic group containing a perfluoroalkyl group of at least 3 carbon atoms which may be separated by an etheric oxygen atom,
$R^1$ is a substituted or unsubstituted monovalent hydrocarbon group of 1 to 8 carbon atoms,
$R^2$ is a monovalent hydrocarbon group containing a carboxylic acid anhydride structure,
$R^6$ is independently hydrogen, Rf, $R^1$, or $R^2$, at least one hydrogen, Rf, and $R^2$ each being contained in a molecule; and
m is a positive integer of at least 3.

7. The organosilicon compound of claim 3, having the formula (4) wherein
$R^4$ is a substituted or unsubstituted monovalent hydrocarbon group of 1 to 8 carbon atoms, Rf is a monovalent organic group containing a perfluoroalkyl group of at least 3 carbon atoms which may be separated by an etheric oxygen atom, $R^1$ is a substituted or unsubstituted monovalent hydrocarbon group of 1 to 8 carbon atoms, $R^2$ is a monovalent hydrocarbon group containing a carboxylic acid anhydride structure, $R^6$ is independently hydrogen, Rf, $R^1$, or $R^2$, at least one hydrogen, Rf, and $R^2$ each being contained in a molecule;

n is a positive integer of at least 1; and $R^7$ is $R^4$.

8. The organosilicon compound of claim 3, having the formula (4) wherein $R^4$ is a substituted or unsubstituted monovalent hydrocarbon group of 1 to 8 carbon atoms, Rf is a monovalent organic group containing a perfluoroalkyl group of at least 3 carbon atoms which may be separated by an etheric oxygen atom, $R^1$ is a substituted or unsubstituted monovalent hydrocarbon group of 1 to 8 carbon atoms, $R^2$ is a monovalent hydrocarbon group of containing a carboxylic acid anhydride structure, $R^6$ is independently hydrogen, Rf, $R^1$, or $R^2$, at least one hydrogen, Rf, and $R^2$ each being contained in a molecule;

n is a positive integer of at least 1; and $R^7$ is a group of the formula (5):

(5)

wherein $R^4$ and $R^6$ are as defined above.

\* \* \* \* \*